United States Patent [19]

Rieker

[11] Patent Number: 5,718,928
[45] Date of Patent: *Feb. 17, 1998

[54] SCREEN FOR PRODUCING A PERFORATED FILM

[75] Inventor: Gregory M. Rieker, Clinton, Ind.

[73] Assignee: Tredegar Industries, Inc., Richmond, Va.

[*] Notice: The term of this patent shall not extend beyond the expiration date of Pat. No. 5,562,932.

[21] Appl. No.: 663,614

[22] Filed: Jun. 14, 1996

Related U.S. Application Data

[63] Continuation-in-part of Ser. No. 259,461, Jun. 14, 1994, Pat. No. 5,562,932.

[51] Int. Cl.$^6$ .................. B29C 51/10; B29C 51/22
[52] U.S. Cl. .................. 425/290; 264/504; 425/388
[58] Field of Search .................. 425/290, 388; 264/504

[56] References Cited

U.S. PATENT DOCUMENTS

| | | | |
|---|---|---|---|
| 2,430,518 | 11/1947 | Mainwal | 428/132 |
| 3,054,148 | 9/1962 | Zimmerli | 264/504 |
| 3,097,787 | 7/1963 | Schur | 428/132 |
| 3,403,422 | 10/1968 | Nakawawa et al. | 425/131.5 |
| 3,703,432 | 11/1972 | Koski | 428/132 |
| 3,709,647 | 1/1973 | Barnhart | 425/224 |
| 3,814,101 | 6/1974 | Kozak | 604/370 |
| 3,929,135 | 12/1975 | Thompson | 128/287 |
| 4,151,240 | 4/1979 | Lucas et al. | 264/504 |
| 4,155,693 | 5/1979 | Raley | 425/363 |
| 4,252,516 | 2/1981 | Raley et al. | 425/290 |
| 4,319,868 | 3/1982 | Riemersma et al. | 425/290 |
| 4,323,069 | 4/1982 | Ahr et al. | 128/287 |
| 4,324,246 | 4/1982 | Mullane et al. | 604/370 |
| 4,324,247 | 4/1982 | Aziz | 128/287 |
| 4,341,216 | 7/1982 | Obenour | 128/287 |
| 4,341,217 | 7/1982 | Ferguson et al. | 604/370 |
| 4,342,314 | 8/1982 | Radel et al. | 128/287 |
| 4,388,056 | 6/1983 | Lee et al. | 425/83.1 |
| 4,509,908 | 4/1985 | Mullane, Jr. | 425/290 |
| 4,535,020 | 8/1985 | Thomas et al. | 428/131 |
| 4,543,299 | 9/1985 | Raley et al. | 428/596 |
| 4,585,156 | 4/1986 | Raley et al. | 228/132 |
| 4,604,156 | 8/1986 | Raley et al. | 264/504 |
| 4,636,161 | 1/1987 | Raley et al. | 425/194 |
| 4,644,623 | 2/1987 | Raley et al. | 29/148.4 |
| 4,741,877 | 5/1988 | Mullane, Jr. | 264/504 |
| 4,846,813 | 7/1989 | Raley | 604/385.1 |
| 4,878,825 | 11/1989 | Mullane, Jr. | 425/290 |
| 4,895,749 | 1/1990 | Rose | 428/132 |
| 4,953,550 | 9/1990 | Dunshee | 128/403 |
| 5,078,710 | 1/1992 | Suda et al. | 604/383 |
| 5,234,650 | 8/1993 | Hagen et al. | 264/176.1 |
| 5,256,007 | 10/1993 | Allen | 405/258 |
| 5,383,870 | 1/1995 | Takai et al. | 604/358 |
| 5,562,932 | 10/1996 | Rieker | 425/290 |

FOREIGN PATENT DOCUMENTS

| | | | |
|---|---|---|---|
| 0172420 | 2/1986 | European Pat. Off. | 604/358 |
| 9309741 | 5/1993 | WIPO | 604/378 |

*Primary Examiner*—Robert Davis
*Attorney, Agent, or Firm*—Emch, Schaffer, Schaub & Porcello Co., L.P.A.

[57] ABSTRACT

A cylindrical screen for perforating a thermoplastic film or sheets has an outer surface and an inner surface. A plurality of outer apertures extend from the outer surface and terminate at a corresponding inner aperture on the inner surface of the screen. The apertures in the outer surface can have the same or a different geometrical shape as the apertures in the inner surface. The apertures form a passageway through the screen. The passageways are disposed at least one angle from about 5° to about 60° with respect to a plane that is disposed substantially perpendicular to the outer surface of the screen to prevent a direct line of sight through the screen.

27 Claims, 8 Drawing Sheets

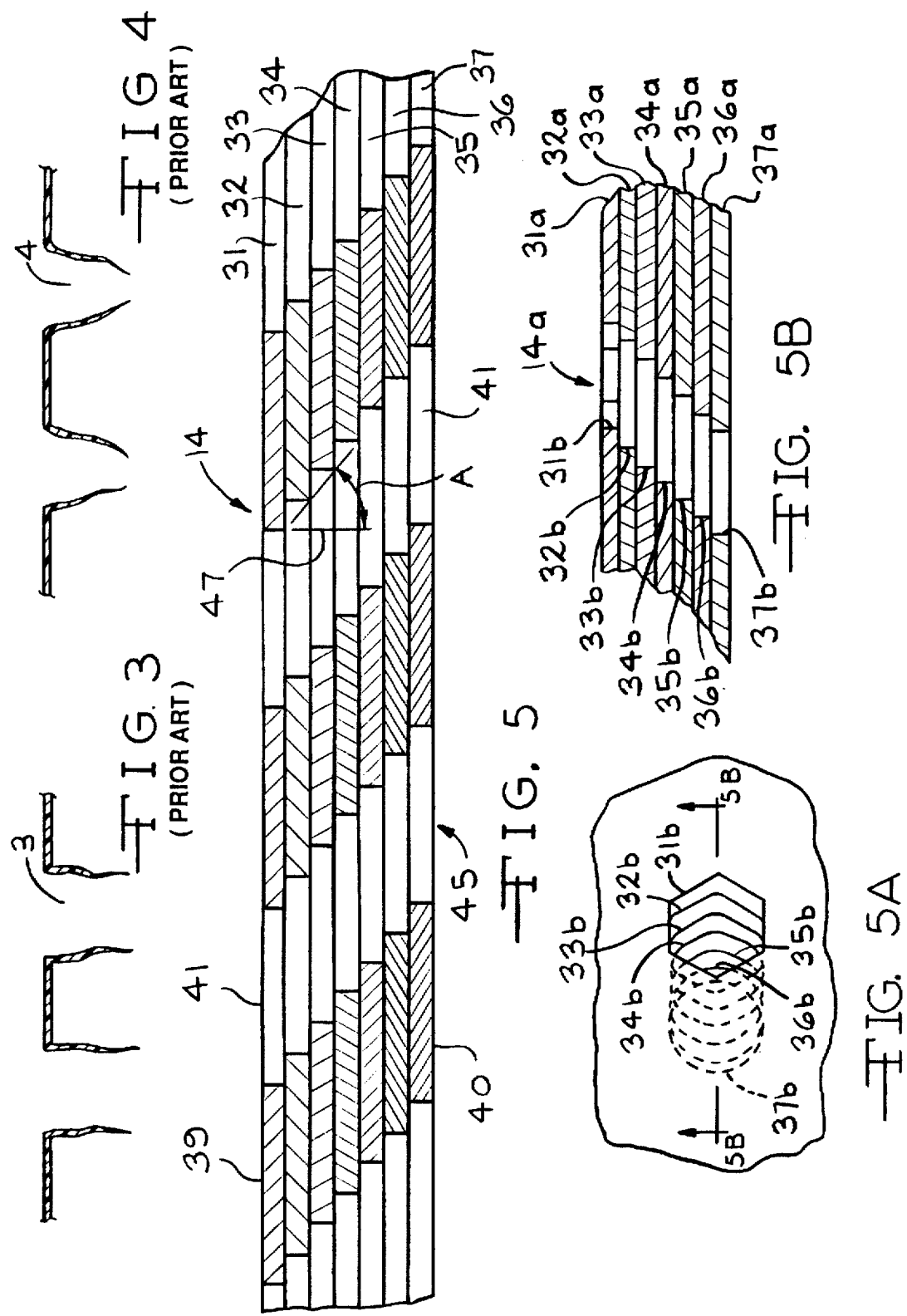

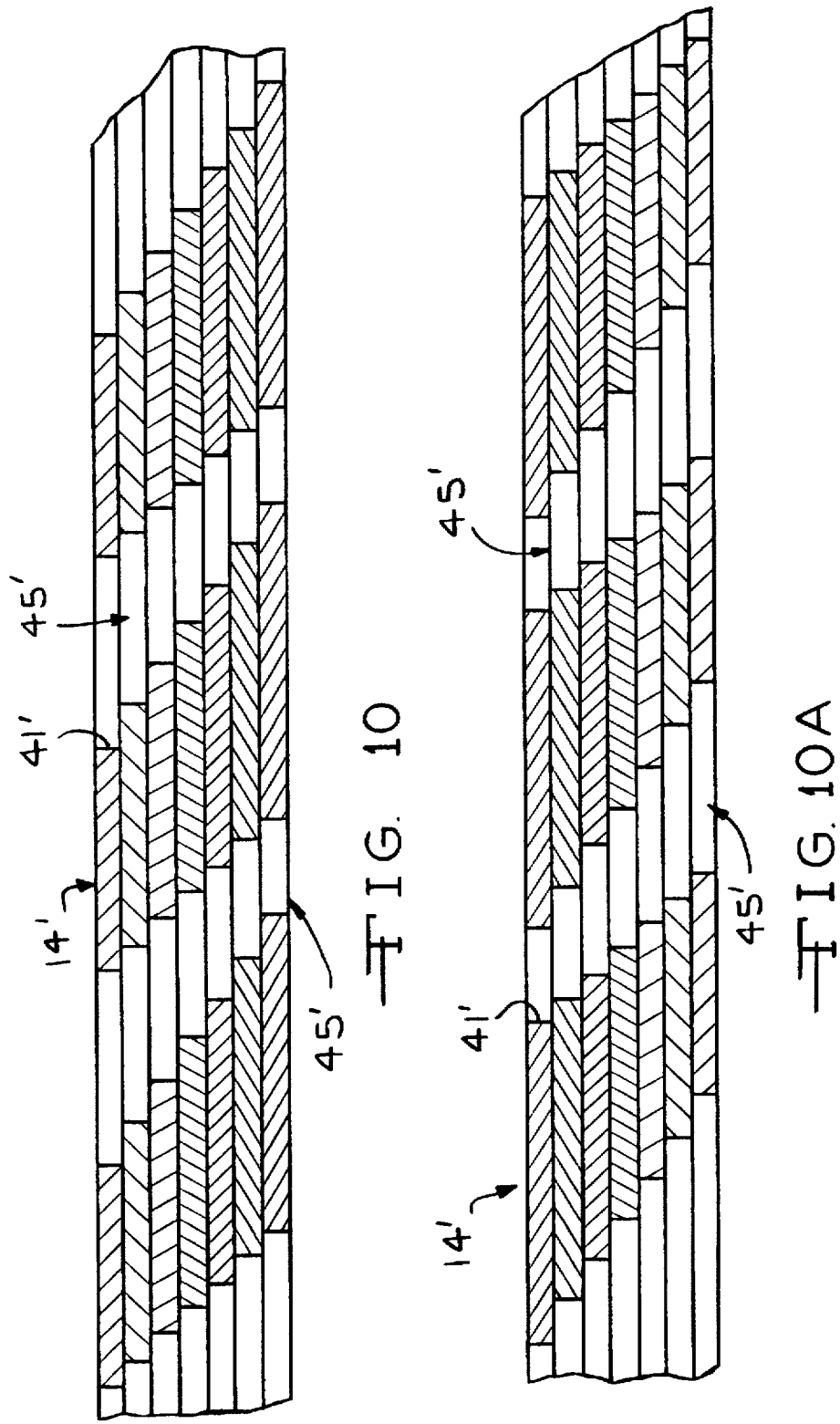

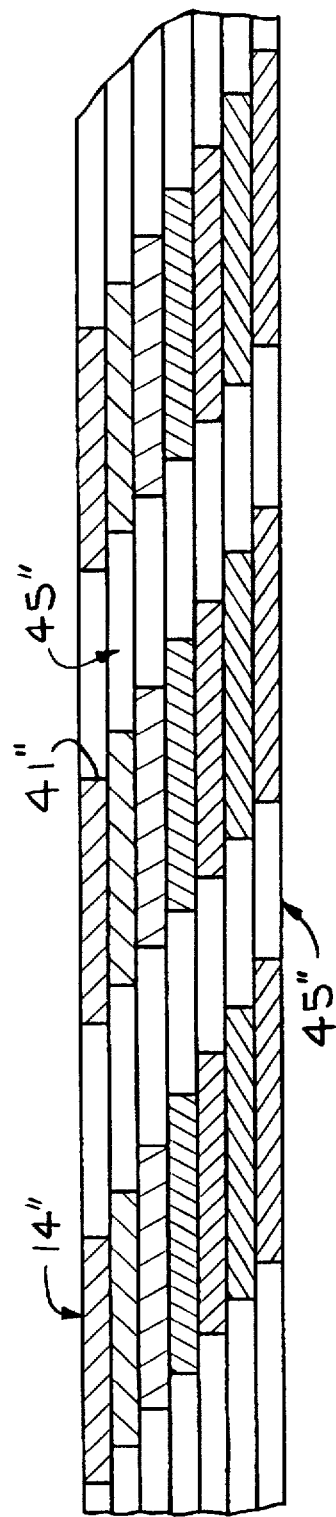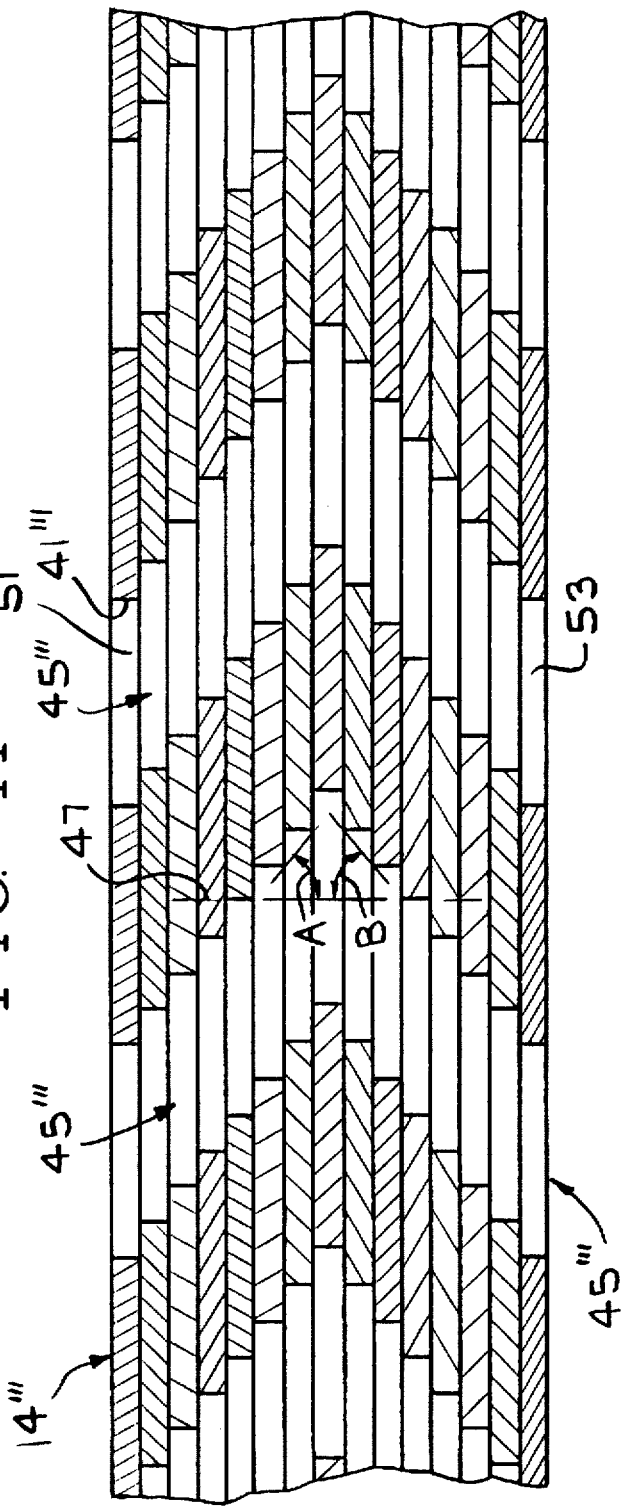

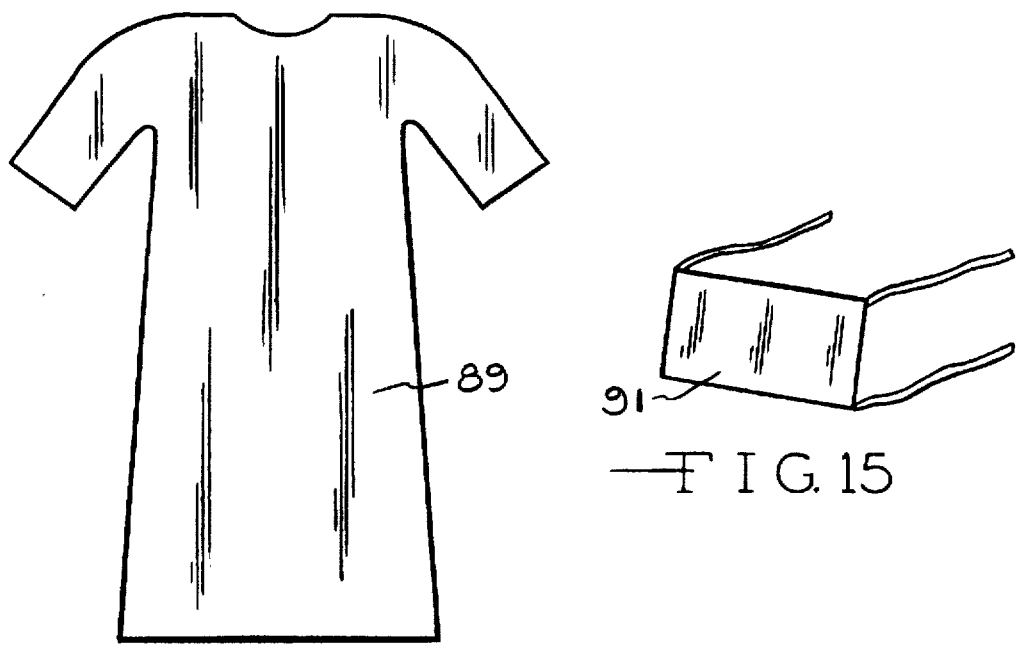
FIG. 14
FIG. 15
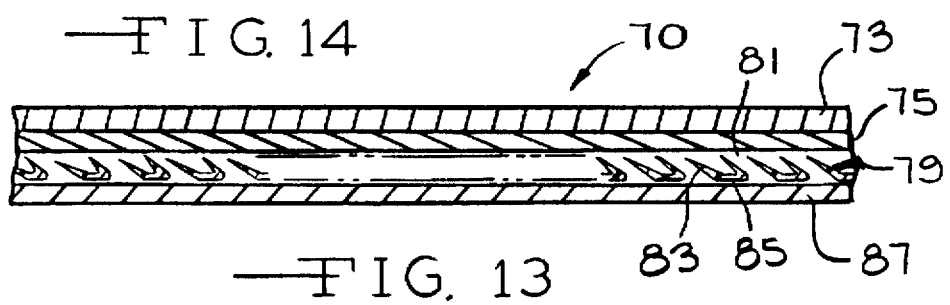
FIG. 13
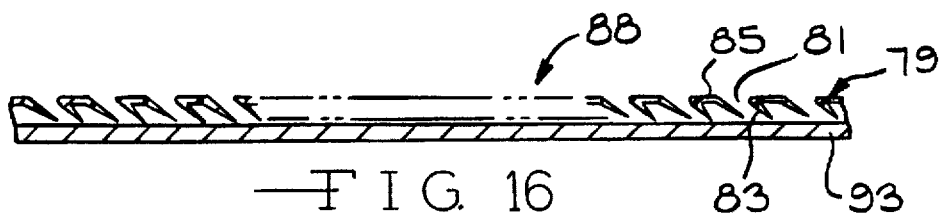
FIG. 16
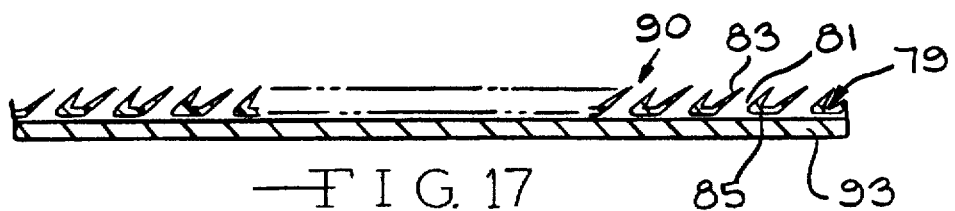
FIG. 17
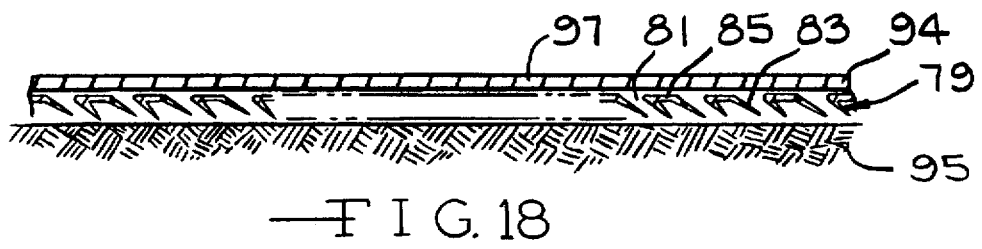
FIG. 18

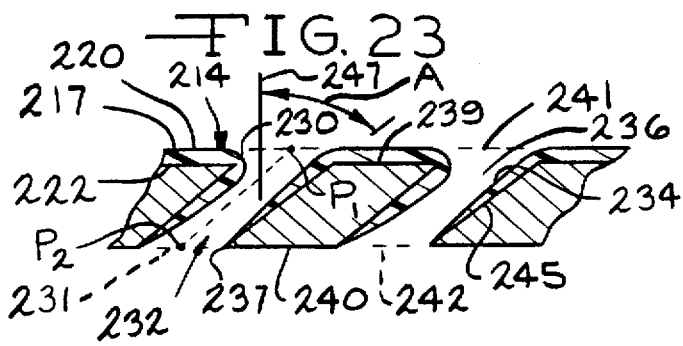
FIG. 23
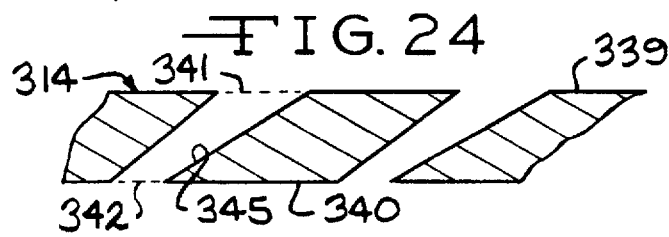
FIG. 24
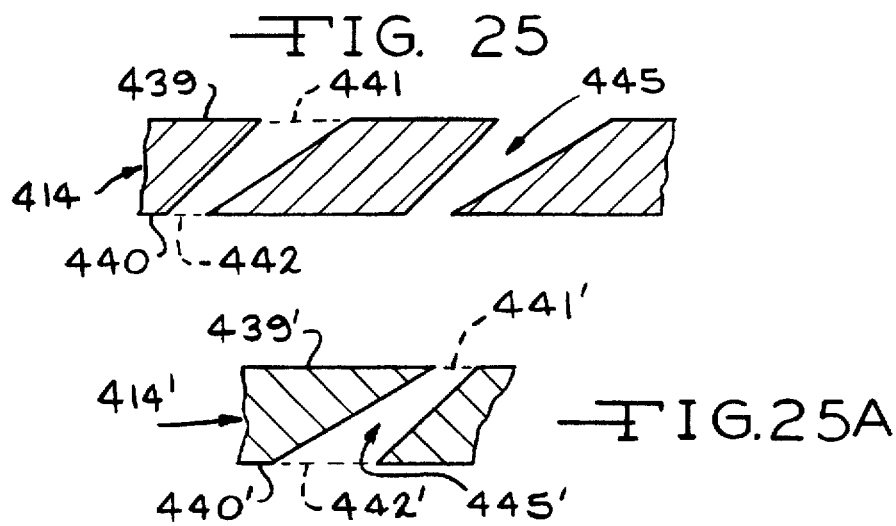
FIG. 25
FIG. 25A
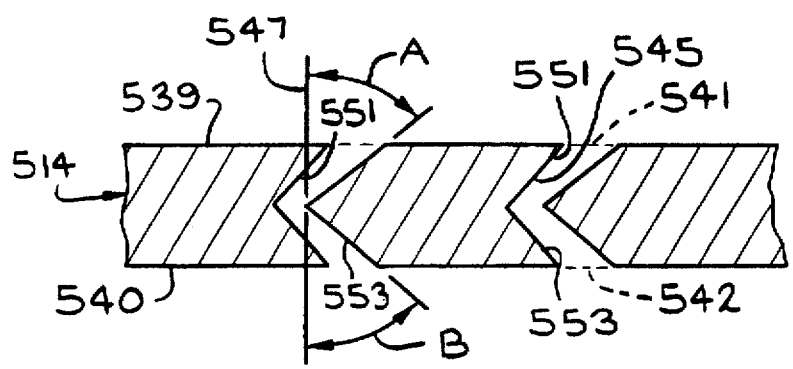
FIG. 26

SCREEN FOR PRODUCING A PERFORATED FILM

The present invention is a continuation-in-part of Ser. No. 08/259,461, filed Jun. 14, 1994, now U.S. Pat. No. 5,562,932 issued Oct. 8, 1996.

BACKGROUND ART

The present invention is in the general field of perforated plastic film and especially relates to perforating of plastic film. The invention particularly relates to perforated plastic film, the metal screens or molding elements used in the vacuum perforation of plastic film and to a method of fabricating such screens.

Perforated plastic film has many useful applications. It is used in gardening and farming to prevent the growth of grass and weeds while permitting moisture to be transmitted through the film to the soil beneath. Perforated films have a multiplicity of regularly spaced apertures which allow permeation of liquid and air or other fluids. Such films can be used as a component of disposable garments for sanitary apparel purposes, such as napkins, diapers, or for hospital pads, bed or sleeping bag linings, and the like. In such composite structures, an exterior layer of film having the desired properties is provided which would be adjacent to the skin in a composite garment, and the garment would also include a filler layer or layers of absorbent fibrous material. An example of the use of perforated film for making disposable diapers is shown in U.S. Pat. No. 3,814,101.

A particular class of perforated film is described by Thompson, U.S. Patent No. 3,929,135, issued Dec. 30, 1975. Thompson teaches an absorptive structure with a top layer of perforated film characterized by having a series of regular spaced small apertures in the form of tapered capillaries of certain dimensions ranges. In the finished article, these are directed inwardly to be in intimate contact with an absorbent fibrous material layer. The smooth side of the perforated film is thus in use in contact with the skin. Film as described by Thompson, in garment structure as outlined, maintains a dry and comfortable condition, even after transmission of fluids to the absorbent layer by the combined effects of the absorption and the resistance to back flow as a result of the relative length and surface properties of the tapered capillaries.

One of the earlier methods for vacuum perforation of plastic film is disclosed in U.S. Pat. No. 3,054,148. The patentee describes a stationary drum having a molding element or screen mounted around the outer surface of the drum and adapted to freely rotate thereon. A vacuum chamber is employed beneath the screen to create a pressure differential between the respective surfaces of the thermoplastic sheet to be perforated to cause the plasticized sheet to flow into openings provided in the screen and thereby cause a series of openings, holes or perforations to be formed in the plastic sheet or film.

One method for making film with tapered capillaries on one side thereof is shown in U.S. Pat. No. 3,054,148 issued Sep. 18, 1962, to Zimmerli. In this patent, heated film is supported by a perforated screen and a vacuum applied to the underside of the perforated screen. Holes are pulled in the film in the direction of the vacuum beneath the screen thereby forming tapered capillaries in the film.

A variety of methods and apparatuses including particular types of perforating screens or rotatable molding elements have been developed over the years for particular perforation operations. Examples of these are U.S. Pat. Nos. 4,878,825; 4,741,877; 4,644,623; 4,636,161; 4,604,156; 4,585,156; 4,543,299; 4,509,908; 4,155,693; 4,252,516; 3,709,647; 4,151,240; 4,319,868 and 4,388,056. In U.S. Pat. Ser. Nos. 4,878,825, 4,741,877 and 4,509,908, the screen comprises a plurality of conically shaped apertures which extend through a plurality of laminae stacked together.

In U.S. Pat. Nos. 4,604,156, 4,543,299 and 4,585,156, the screens described therein each define a plurality of holes extending therethrough whose walls are substantially straight and perpendicular.

In U.S. Pat. Nos. 4,636,161 and 4,644,623 the screens defined therein comprise multiple layers of thin sheets having various hole sizes which overlap in a random manner to produce films having non-apertured portions and apertured portions.

In U.S. Pat. No. 4,155,693 the screen comprises a series of perforated metal strips preferably welded together to form a cylinder. U.S. Pat. No. 4,252,516 provides a screen having a series of hexagonal depressions with elliptical holes centered therein. U.S. Pat. No. 3,709,647 provides for a rotating vacuum-forming roll having a circulating cooling medium therein.

U.S. Pat. No. 4,151,240 provides a means for cooling the film after it has been perforated and debossed. U.S. Pat. No. 4,319,868 sets forth an apparatus for making a thermoplastic film having raised bosses with perforated tips. A particularly constructed embossing roll for effecting the desired film pattern is disclosed. U.S. Pat. No. 4,388,056 discloses an apparatus for continuously forming an air-laid fibrous web having oppositely phased, cylindrically undulating side edges and a predetermined basis weight distribution. An air-laying drum has a honeycomb-type annular-shape frame including circumferentially extending ribs and transverse plates. A stationary adjustable air flow modulating means is disposed adjacent the radially inwardly disposed boundary of an arcuate portion of a circumferentially segmented annular-shape plenum, circumferentially spanning a plurality of plenum segments for adjusting a pressure drop across particular areas of the surface of the air-laying drum.

Vacuum perforation of thin plastic films involves the extrusion of molten polymeric materials such as polyethylene and other plastic polymers through a die. The hot melt web of film or plastic sheet exiting the die impinges on a rotating cylindrical screen which is mounted on a stationary vacuum drum or roll. The vacuum roll has an axial slot and a set of seals extending longitudinally along the length of its inside surface, beneath the area where the web of plastic impinges on the screen or molding element. A vacuum from inside the screen is directed through the slot in the vacuum roll. The vacuum present within the slot forms or molds the plastic film or sheet to the screen and perforates it through the holes of the screen. At the same time, an airflow is produced which cools the film.

An important component of the vacuum processing equipment is the cylindrical screen. This molding element defines aesthetic, tactile and mechanical properties of the film as well as the geometric pattern of the perforated film. In a preferred screen fabrication technique, the desired screen pattern is nickel plated on a specially prepared cylindrical mandrel. A seamless cylindrical nickel screen of any predetermined or desired pattern can be produced. Other metals, such as copper may also be used.

However, the prior art screens produce film with perforations that extend through the film at substantially a right angle to the surface of the film. Such perforations provide a direct line of sight and a direct path through the film. This feature of the prior art film is undesirable when the film is used in catamenial or incontinent applications as the collected fluid remain visible. Accordingly, there is a need for a perforated film having masking characteristics that reduce the visible presence of the collected fluids.

It is also desirable to have a film that does not provide a direct path through the film for fluids. Such a film can be utilized for protective clothing as fluids contacting the surface of the film will not have a direct path through the film. Such a characteristic greatly improves the protective quality of the clothing.

DISCLOSURE OF THE INVENTION

The invention is directed to a cylindrical screen for perforating a thermoplastic film or sheet. In certain embodiments, the screen is formed from a single thickness of material while in other embodiments, the screen is formed of a plurality of thin layers. In both embodiments, the screen can be formed by being secured or welded at its ends to form a seamed, cylindrical shape. In certain other embodiments, the screen can be formed in a seamless manner by using a suitable method such as an electroplated screen forming method, plasma spray method, or the like.

The screen has a first, outer surface and a second, inner surface. A plurality of apertures extend through the screen from the first surface to the second surface. (It is to be noted that, in the embodiments where the screen comprises a plurality of layers, each layer contains a plurality of apertures which are at least partially in communication with apertures in adjacent layers). Each aperture forms a passageway through the screen. The passageways are disposed at an angle from about 5° to about 60° with respect to a plane that is disposed substantially perpendicular to the surface of the screen. The passageways prevent a direct line of sight from an outside surface of the screen to an inside surface of the screen. In certain embodiments, the apertures in the first surface of the screen (and in each adjacent layer in embodiments comprising a plurality of layers) can have a geometrical shape which differs from the geometrical shape of the apertures in the second surface of the screen (and in the adjacent layers in the multi-layer embodiment).

BRIEF DESCRIPTION OF THE DRAWINGS

FIG. 3 is an enlarged, schematic, sectional view of a prior art perforated film having straight capillaries.

FIG. 4 is an enlarged, schematic, sectional view of a prior art perforated film having tapered capillaries.

FIG. 5 is a cross-sectional view of a film forming screen of the present invention.

FIG. 5A is a plan view, partially in phantom, of a film forming screen.

FIG. 5B is a cross-sectional view, taken along the line 5B—5B in FIG. A.

FIG. 10 is a cross-sectional view of a film forming screen.

FIG. 10A is a cross-sectional view of a film forming screen.

FIG. 11 is a cross-sectional view of a film forming screen.

FIG. 12 is a cross-sectional view of a film forming screen.

FIG. 13 is a cross-sectional view of a fabric containing the perforated film of the present invention.

FIG. 14 is a protective gown using the fabric of FIG. 13.

FIG. 15 is a facemask using the fabric of FIG. 13.

FIG. 16 is a cross-sectional view of an absorbent pad or drape.

FIG. 17 is a cross-sectional view of an absorbent pad or drape.

FIG. 18 is a cross-sectional view of a landscape fabric.

FIG. 23 is a cross-sectional view of a film forming screen and a film being formed thereon.

FIG. 24 is a cross-sectional view of a film forming screen.

FIG. 25 is a cross-sectional view of a film forming screen.

FIG. 25A is a cross-sectional view of a film forming screen.

FIG. 26 is a cross-sectional view of a film forming screen.

BEST MODE OF CARRYING OUT THE INVENTION

Figure 1:
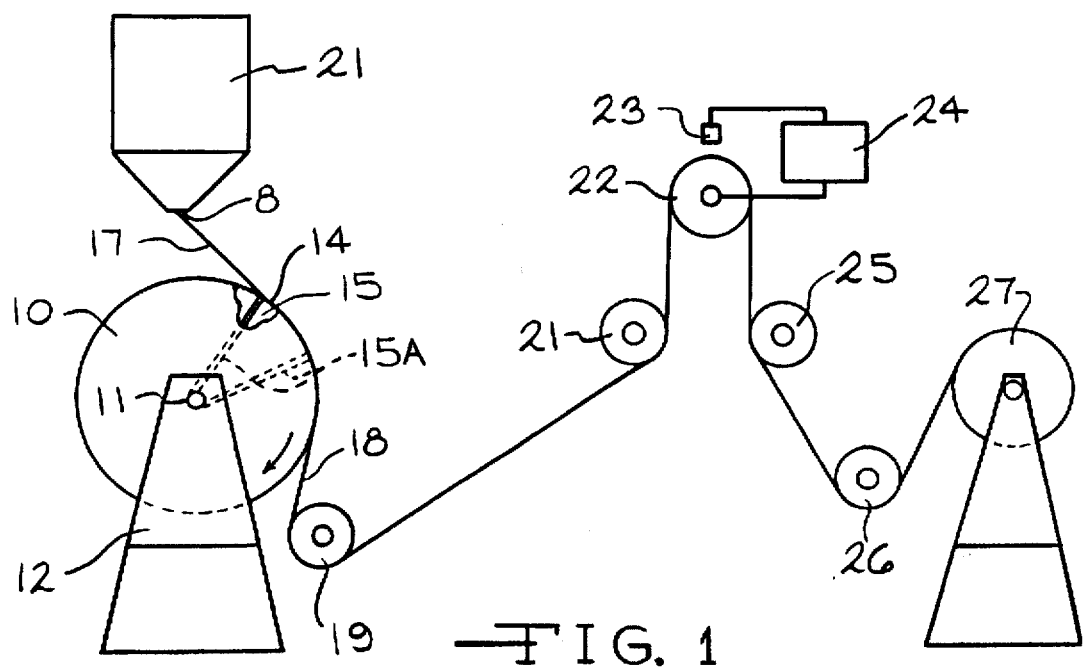
FIG. 1 is a schematic elevational view showing the interrelationship of the principle pieces of equipment employed in carrying out the process.

Referring to FIG. 1, an apparatus for carrying out the process of the invention includes a rotary cylindrical drum 10 supported at each end by a centrally disposed axle 11 supported by means of stationary axle supports 12. The cylindrical surface 13 of drum roll 10 is highly perforated to allow air to pass therethrough. The molding element or screen 14 is mounted around the surface 13 of drum 10 and is adapted to rotate with the drum 10.

Element 14 may be formed as an integral unit adapted to be slipped on drum 10 from an end thereof or it may be wrapped around the drum 10 and then affixed thereto in any suitable manner. For purposes of rotating drum 10, a gear drive may be employed which is adapted to mesh with gearing provided on the drum element itself or a pulley drive may be connected to the drum by means of caps provided on the ends thereof. As shown in FIG. 1, a vacuum chamber 15 is utilized to create a pressure differential between the respective surfaces of the thermoplastic sheet to cause the plasticized sheet to flow into the perforations provided in the molding element 14 and therefore perforate the sheet.

Figure 2:
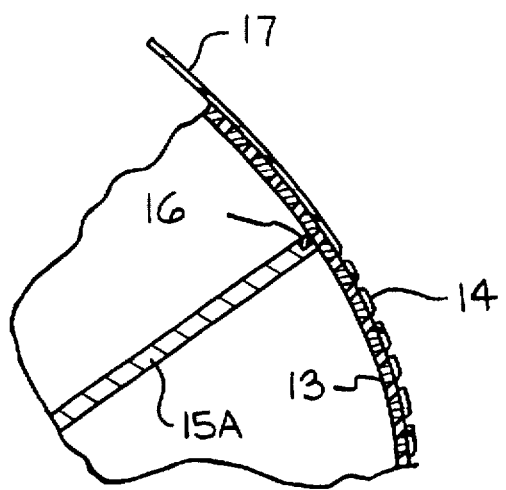
FIG. 2 is an enlarged, sectional view showing a segment of the forming surface as employed in the process.

Referring to FIGS. 1 and 2, the vacuum chamber 15 is positioned within drum 10, along the axis of drum 10 and opens at the surface of the drum over a limited portion of its periphery in contact with the inner portion of surface 13 of drum 10. Two plates 15A define the chamber. In order to provide an effective seal of the leading and trailing edges of chamber 15, seals 16 are provided in plates 15A to form a seal against the surface 13. The seals may be made of metal, HDPE, rubber or other suitable material. The plates 15A are stationary with respect to the rotational direction of the drum and rigidly affixed to axle 11 or other suitable means so that chamber 15 remains in a fixed or stationary position in drum 10. Thus, chamber 15 is sealed at all points except the peripheral openings on drum 10 and may be evacuated or reduced in pressure by pumping equipment connected to the chamber in any suitable manner.

As can be seen in FIG. 1, located above and adjacent to drum 10 is extruder 21 having a die 8 which is used to extrude a hot thermoplastic sheet 17 onto drum 10. In practice it has been found that polyolefin materials work particularly well as the thermoplastic material that is extruded onto the drum 10. As the sheet material 17 travels downwardly from die 8, the sheet contacts screen 14 which is turning clockwise with drum 10 in FIGS. 1 and 2. The rotating screen 14 carries sheet 17 over vacuum slot 15 which causes the thermoplastic material to be drawn into the openings in screen 14 and thereby perforated. The sheet is cooled to change the hot thermoplastic material from its molten state to a solid state and to set the perforations in the film. The sheet 17 continues to travel around in a clockwise manner shown in FIG. 1 on drum 10 and continues on to the rolls 19.

From roll 19 the solid sheet material 18 continues upwardly over roll 21 to corona treating roll 22. The corona treating roll 22 is usually covered with a suitable dielectric material such as epoxy, fluorinated polyethylene (TEFLON®), chlorinated polyethylene (HYPALON®), or polyester (MYLAR®). However, bare roll treating with a dielectric covered electrode can be utilized to treat the film. The electrode or corona bar 23 is suspended parallel to the treater roll at about 1/16 of an inch above the roll. The corona bar 23 is energized by a transformer and corona treating power source 24. The sheet continues past a tension roll 25 to a second tension roll 26 and onto wind-up roll 27. It should be understood that the corona treating operation is not required for all applications for the film and this part of the process can be removed. Further, it is not always necessary to wind the film onto a wind-up roll 27 if the film is being put into an end use application in an in-line process.

It should be noted that other forming processes can be utilized to form the perforated plastic films of the present invention. The process shown in U.S. Pat. No. 4,878,825 which utilizes a support for the forming screen in the area of the vacuum slot works particularly well in forming the perforated film of the present invention. The process shown in U.S. Pat. No. 4,839,216 that utilizes a high-pressure liquid stream to perforate a plastic film can be also used with the present invention. The teachings of U.S. Pat. Nos. 4,878,825 and 4,839,216 are hereby expressly incorporated by reference into this patent application as alternative methods for forming the perforations of the present invention.

FIGS. 3 and 4 show prior art types of perforated plastic films that have been produced on the apparatus shown in FIG. 1. This film has straight capillaries 3 as shown in FIG. 3, or tapered capillaries 4 as shown in FIG. 4. In both of these films, the perforations are disposed at substantially a 90° angle with respect to the surface of the film and provide a direct line of sight and a direct path through the film.

One configuration for the screen 14 of the present invention which is utilized to form the perforated plastic film is shown in more detail in FIG. 5. The screen 14 is a laminate structure comprised of a stack of individual sheets 31, 32, 33, 34, 35, 36, and 37. The screen 14 has an outer surface 39 that is disposed to be in contact with the thermoplastic sheet 17 and an inner surface 40 that faces the vacuum chamber 15. The sheets contain a plurality of apertures 41 that extend through the thickness of the individual sheets. In the embodiments shown in FIG. 5, the apertures 41 all have substantially the same geometric shape; however, it should be understood that the shapes of the apertures can be different. For example, the apertures 41 in adjacent sheets can each have a slightly different geometrical shape. FIG. 5A and 5B show one embodiment wherein a multi-layer screen 14a comprises a plurality of individual sheets 31a, 32a, 33a, 34a, 35a, 36a and 37a. Each sheet comprises a plurality of apertures that extend through the sheet. The sheet 31a comprises a plurality of apertures 31b, each of which has a substantially hexagon shape. The adjacent sheet 32a has a plurality of apertures 32b, each of which has a slightly different shape or a somewhat "rounded" hexagon shape. Each subsequent adjacent sheet 33a through 37a also has a plurality of apertures 33b through 37b which slightly differ in shape from apertures in the adjacent sheets. The apertures 37b have a substantially circular shape.

The sheets are normally a stainless steel, photo-etched metallic material where the photo-etching has formed the apertures 41 in the individual sheets. The sheets generally have a thickness from about 1 to about 5 mils. In practice it has been found that sheets having a thickness of about 2 mils work particularly well. Usually from about 2 to about 20 sheets are used to form the screen 14. The preferred range for the number of sheets to form a screen 14 is from about 4 to about 10 sheets. The effective diameter of the apertures 41 in the sheets is from about 2 mils to about 100 mils. In practice it has been found that a range from about 7 mils to about 60 mils for the effective diameter of the apertures 41 works particularly well. The sheets comprising the laminate are bonded to one another at contact points while the laminate is subjected to heat and pressure. The resultant laminate structure is thereafter rolled into a tubular shape and its free edges are bonded to one another to form a continuous tubular-forming structure. As shown in FIG. 5, the apertures 41 in the laminate structure are not concentrically aligned. Instead, the apertures 41 are circumferentially displaced in the same direction to form a passageway 45 through the laminate structure that is disposed at an angle. The apertures 41 shown in FIG. 5 all have substantially the same diameter and each aperture has been displaced from about 1% to about 50% of the diameter of the apertures from the aperture on the adjacent sheet with a preferred range of displacement for adjacent apertures is about 5% to about 25% of the diameter of the apertures. In practice it has been found that a displacement of about 10% of the diameter of the apertures works particularly well. This results in a passageway 45 that is disposed at an angle from about 5° to about 60° with respect to a plane or line 47 which extends perpendicular to the outer surface 39 of the screen 14. This angle is generally shown as angle A in FIG. 5.

As shown in FIG. 5, the apertures 41 in the sheets are generally circular in shape and the passageway 45 formed through the laminate screen 14 is generally cylindrical in shape. However, it should be understood that shapes for the apertures can vary in each layer of the screen and can also vary in shape from layer-to-layer (as shown above with respect to FIGS. 5A and 5B). It is to be further understood that oval, ellipsoidal and other shapes can be used, and multi-sided figures such as a rectangle, square, hexagon or a pentagon can be utilized for the apertures in the sheets.

As shown in FIG. 10, the screen 14' has apertures 41' that become progressively smaller in each adjacent sheet of the laminate. In this screen structure, the passageway 45' that is formed will converge as the passageway advances through the screen 14'. In this particular structure each aperture 41' is displaced a selected percentage of its diameter from the apertures on adjacent sheets. This results in a passageway 45' that continuously and uniformly converges as the passageway advances through the screen 14'.

As shown in FIG. 10A, the screen 14' has apertures 41' that become progressively larger in each adjacent sheet of the laminate. In this screen structure, the passageway 45' that is formed will diverge as the passageway advances through the screen 14'. In this particular structure, each aperture 41' is displaced selected percentage of its diameter from the apertures on adjacent sheets. This results in a passageway 45' that continuously and uniformly diverges as the passageway advances through the screen 14'.

The screen 14" shown in FIG. 11 has apertures 41" that become progressively smaller as the apertures shown in FIG. 10. However, in FIG. 11, the apertures 41" are displaced in the screen 14" as that the passageway 45" converges in one direction as the passageway advances 5through the screen 14".

As shown in FIG. 12, the screen 14'" defines a passageway 45'41 that has a compound curve for the passageway. In this embodiment a portion of the sheets that form the screen 14'" are displaced in one direction to form a first portion 51 of the passageway 45'" and a plurality of sheets are displaced in the opposite direction to form a second portion 53 for the passageway 45'". In certain embodiments, all of the apertures 41'" will be of the same diameter and will be displaced a equal distance on each layer of the screen 14'". However, it should be noted that the apertures 41'" can vary in size and/or shape and the amount of displacement can vary to form a converging passageway 45'". In the embodiments shown in FIG. 12, the first portion 51 of the passageway 45'" is disposed at an angle A that is from about 5° to about 60° with respect to a line or plane 47' which extends perpendicular to an outer surface 39'" of the screen 14'". The second portion 53 is disposed at an angle B that is from about 5° to about 60° with respect to the plane or line 47.

Figure 6:
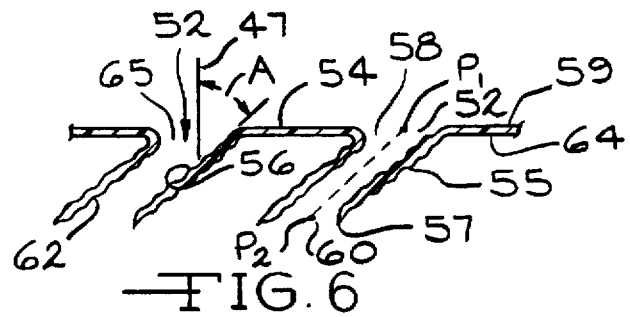
FIG. 6 is a cross-sectional view of a perforated film made using the screen of FIG. 5.

FIG. 6 shows a cross section of a film 54 that has been formed utilizing the screen shown in FIG. 5. The film 54 has a first surface 59 and a second surface 64. The first and second surfaces of the film are usually positioned in substantially parallel relationship. The film 54 has a plurality of perforations 52 that form angled capillaries 55 which extend 15 from the second surface 64. In the embodiment shown in FIG. 5, the capillaries 55 have a substantially uniform diameter such that the capillary 55 has a substantially cylindrical shape. However, as seen below, in other embodiments, the capillaries can have diameters which gradually change, increase or decrease as the capillary extends from the second surface 64. Each capillary 55 is displaced at an angle A from about 5° to about 60° : with respect to a plane 47 that is perpendicular to the first surface 59 of the film. Each capillary 55 has a first opening 58 in the first surface 59 of the film 54 and at least one side wall 62 which defines a passageway 65 through the capillary 55. The capillary 55 also has a second opening 60 at an end 57 of the capillary 55 that is spaced apart from the second surface 64 of the film 54. In preferred embodiments, the ends 57 of the capillaries 55 are usually spaced apart from the first surface 59 of the film 54 by a distance from about 0.005 to about 0.05 of an inch with a spacing from about 0.007 to about 0.025 of an inch being preferred. The opening 58 and the opening 60 both have a center point or geometric center ($P_1$ and $P_2$, respectively). The center point $P_1$ of opening 58 is displaced from the center point $P_2$ of opening 60 by a distance that is from about 5% to about 200% of the diameter of the opening 60. The preferred range of displacement is from about 75% to about 125% of the diameter of the opening 60. As can be seen in FIG. 6, the capillaries 55 have a plurality of steps or ridges 56 that are produced by the off-set sheets of the screen 14. The ridges 56 in the film 54 are substantially rounded instead of the sharp corners formed by the off-set sheets that form the screen 14.

Figure 9:
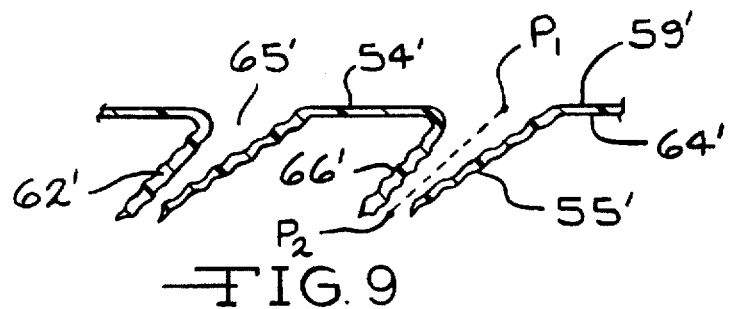
FIG. 9 is a cross-sectional view of a perforated film made using the screen of FIG. 10.

FIG. 9 shows the cross section of a film 54' that has been formed utilizing the screen shown in FIG. 10. This film 54' is substantially similar to the film shown in FIG. 6 except that the side wall 62', each capillary 55' and the passageway 65' converge as it extends from the first surface 59' of the film.

Figure 7:
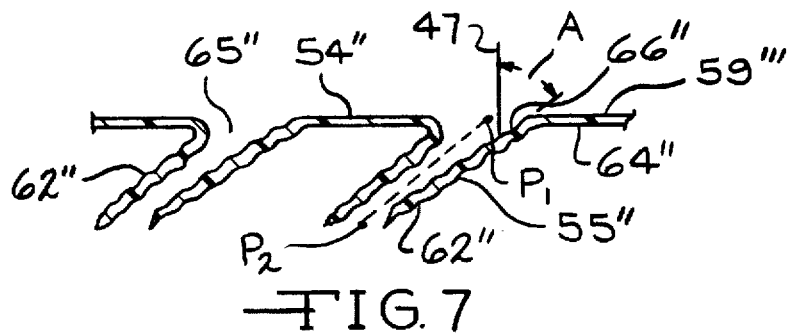
FIG. 7 is a cross-sectional view of a perforated film made using the screen of FIG. 11.

FIG. 7 shows a cross section of a film 54" that has been produced using the screen in FIG. 11. In this film the side wall 62" of the capillaries 55" and the passageway 65" converges as it advances away from the surface of the film and in particular converges on one side in one direction.

Figure 8:
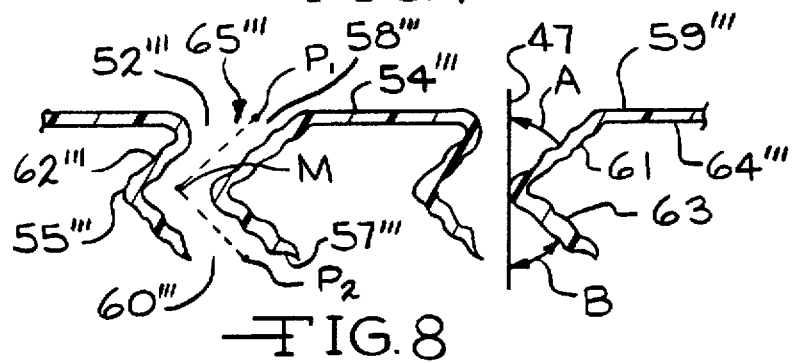
FIG. 8 is a cross-sectional view of a perforated film made using the screen of FIG. 12.

FIG. 8 shows a cross section of a section of film 54'" produced utilizing the screen shown in FIG. 12. The film 54'" has a first surface 59'" and a second surface 64'". The first and second surfaces 59'" and 64'" of the film 54'" are usually positioned in substantially parallel relationship. The film 54'" has a plurality of perforations 52'" that form angled capillaries 55'" which extend from the second surface 64'". In this figure the capillaries 55'" and the passageway 65'" have a first portion 61 that is disposed at an angle A with respect to a plane 47 that is disposed perpendicular to the first surface 59'" of the film and a second portion 63 that is disposed at an angle B. The first portion 61 and the second portion 63 are adjacent each other at a midpoint M. The capillary 55'" has a first opening 58'" in the first surface 59'" of the film 54'" and a second opening 60'" at an end 57'" of the capillary 55'" that is spaced apart from a second surface 64'" of the film 54'". The first opening 58'" has a centerpoint $P_1$ that is displaced from the midpoint M. The second opening 60'" has a center point $P_2$ that is displaced from the midpoint M. A first centerline extends between the centerpoint $P_1$ and the midpoint M and a second centerline extends between the midpoint M and the centerpoint $P_2$. In the embodiment shown in FIG. 8, both angles A and B are from about 5° to about 60° with respect to the plane 47. In FIG. 8 the capillary 55'" generally converges as it advances from the first surface 59'" of the film 54'". However, it should be understood that the capillaries 55'" can have walls that do not converge and that are substantially parallel.

The above films all have capillaries that are disposed at an angle that acts to block a direct line of sight through the apertures that is perpendicular to the surface of the film. Accordingly, the films will have a masking characteristic such that fluids that pass through the film to an absorbent structure will not be as visible to a user as when the capillaries are perpendicular to the first surface 59 of the film. This is particularly important for catamenial or incontinent applications. The degree of masking produced by the film will be directly proportional to the angle of the capillaries in the film, their length and the degree to which the capillaries converge in shape. Such films also can be useful in preventing unwanted direct fluid flow through the film. Since the capillaries are disposed at an angle, fluid striking the surface of the film will not have a direct path through the film. Instead, the fluid will have to change direction to pass through the capillaries. Such film can be used for protective clothing when fluids may come into direct contact with the surface of the protective clothing. The film of the present invention will reduce the tendency of the fluid from splashing directly through the capillaries and greatly enhance the protective capability of the clothing.

FIG. 13 shows a layered fabric material 70 that utilizes the film of the present invention. The layered fabric material 70 has a light weight, breathable outer layer 73. The outer layer 73 is usually a paper cover stock that is very light weight and also highly breathable. Next is a layer of non-woven material 75 that is breathable, but provides resistance to the passage of fluids through this layer. In particular, the non-woven material provides good resistance to flow for liquids that come in contact with the non-woven material. A melt blown polypropylene, polyethylene or polyester can be used for the non-woven layer as these materials have acceptable levels of fluid resistance. The next layer on the fabric material 70 is a thermoplastic film 79 that has a plurality of perforations 81. The perforations form capillaries 83 which are disposed at an angle from about 5° to about 60° with respect to a plane that is perpendicular to a first surface 85 of the film. The thermoplastic film 79 is positioned so that the capillaries 83 extend toward and are in contact with the nonwoven material 75. The capillaries 83 formed by the perforations 81 allow the film 79 to be breathable while resisting the direct flow of liquid through the film. Although the film 79 has been shown as being substantially similar to the film 54 shown in FIG. 6, it should be understood that the film similar to the films shown in the other Figures herein, can also be used for the film 79 in the layer fabric material 70. The next layer in the layered fabric 70 is a second layer of non-woven material 87 that is positioned adjacent the surface 85 of the film 79. The second layer of non-woven material 87 is intended to be a layer that comes into contact with the skin of the user of the fabric material 70. If the fabric material is not intended to come into contact with the skin of the user, the second layer of non-woven material 87 can be deleted. The purpose of the fabric material 70 is to provide a breathable structure that has good resistance to penetration to fluids and more particularly, liquids. The fabric 70 is intended to be used in applications where fluids are splashed or sprayed onto the material and the material provides resistance to the direct pass through of a fluid. This fabric can be utilized in the medical field, hazardous waste field or other areas where people are interested in being protected from spilled or sprayed fluids.

FIG. 14 shows a protective gown 89 and FIG. 15 shows a protective facemask 91 that can be made using the layered fabric material 70. For the protective gown 89, the second layer of non-woven material 87 may be deleted if the gown is to be worn over clothes so that the inner surface of the gown does not contact the skin of the wearer. For both the protective gown 89 and the facemask 91, fluids that are spilled or sprayed will contact the outer layer 73 of the fabric. The fluid will pass through to the non-woven material 75 which provides resistance to fluid penetration. The fluid will then contact the thermoplastic film 79 having the angled capillaries 83. When the fluid engages the thermoplastic film 79, there is no direct path through the film and the velocity of the fluid is significantly reduced. The structure of the layered fabric 70 is intended to prevent direct passage of fluids and provides a much higher level of protection than the breathable materials that are currently available.

FIG. 16 shows the use of the thermoplastic film of the present invention in an absorbent pad or drape 88. In the structure, the film 79 is positioned on a layer of absorbent material 93. The film 79 is disposed so that the capillaries 83 that are formed by the perforations 81 are in contact with the absorbent material 93. With the structure the capillaries 83 act to wick fluid that is on a first surface 85 of the thermoplastic film 79 to the absorbent material 93. The angled capillaries 83 prevent a direct line of sight along a line that is perpendicular to the surface 85 of the film into the absorbent material 83 so that fluids that are contained in the absorbent material 83 are not easily visible when looking at the surface 85 of the film 79.

FIG. 17 shows another embodiment of a pad or drape 90 that can be made utilizing the film of the present invention. The film 79 is positioned with a first surface 85 of the film in contact with a layer of absorbent material 93. The film 79 is positioned so that the capillaries 83 formed by the perforations 81 extent in a direction away from the absorbent material 93. With the capillaries 83 extending away from the absorbent material 93, there is more resistance to strike through for a liquid that is under pressure, such as a sprayed or spilled liquid.

FIG. 18 shows the use of the thermoplastic film 79 as a landscape fabric 94. In this application, the film is positioned with the capillaries 83 extending towards the ground 95 upon which the film is to be positioned. The perforations 81 and the capillaries 83 allow moisture, such as rain, to pass through the film to the ground 95. However, the angled capillaries 83 effectively eliminate or minimize the amount of light that can pass through the film 79. This prevents weed growth and other undesirable growth in areas where the film is positioned. However, since rain can pass through the film, there is no difficulty with disposing of or pooling of rain water. In applications where additional strength is required, a non-woven material 97 can be laminated to the surface 85 of the film 79 to provide additional strength. It should also be understood that the non-woven material 97 can also be laminated to the opposite side of the film 79 to provide additional strength to the landscape fabric 94.

Figure 19:
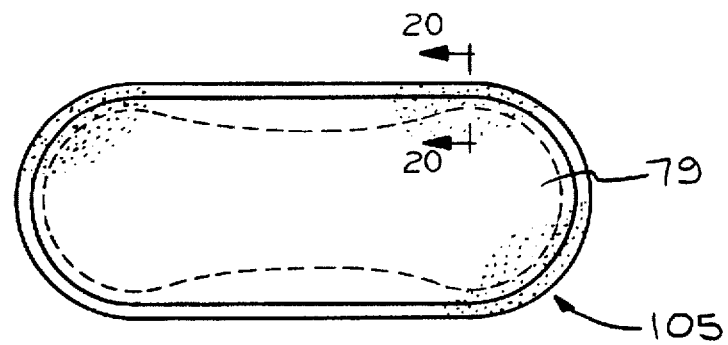
FIG. 19 shows a catamenial pad construction using the film of the present invention.
Figure 20:
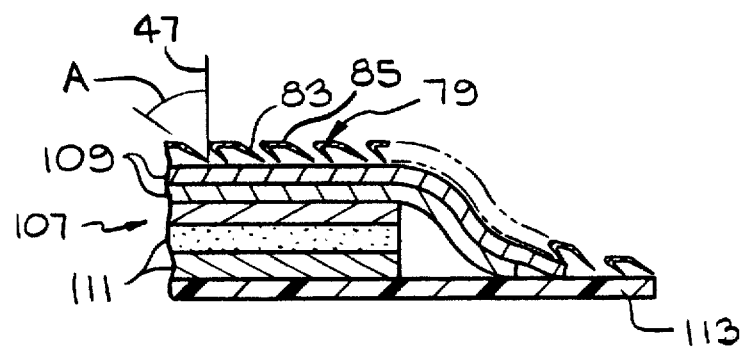
FIG. 20 is a cross-sectional view taken along line 20—20 in FIG. 19.

FIG. 19 and 20 show a catamenial or feminine hygiene pad 105 that can be constructed using the film of the present invention. The pad 105 has a layer of perforated thermoplastic film 79 that is positioned over an absorbent core 107. The film 79 is positioned so that the ends of the capillaries 83 that extend from film are in contact with the absorbent core 107. The absorbent core 107 can include one or more layers of a non-woven material 109 and a highly absorbent wadding or gel material 111. A non-pervious thermoplastic film 113 is positioned on the side of the absorbent core 107 that is opposite to the film 79.

Figure 21:
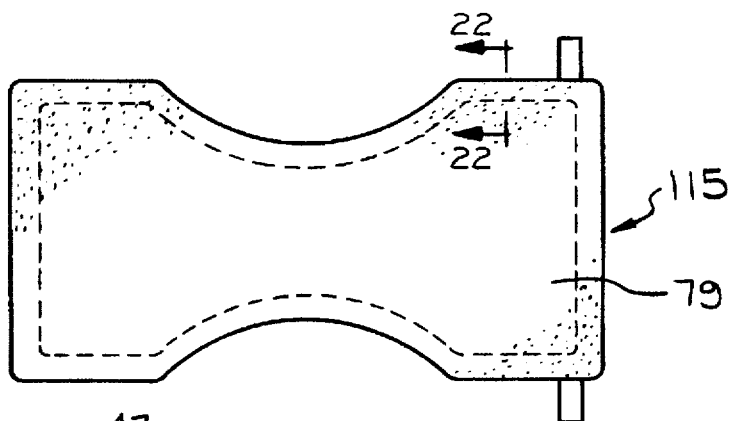
FIG. 21 shows a diaper construction using the film of the present invention.
Figure 22:
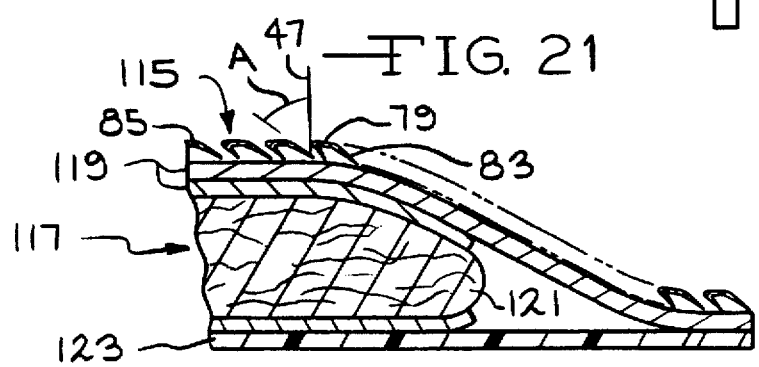
FIG. 22 is a cross-sectional view taken along line 21—21 in FIG. 21.

FIGS. 21 and 22 show a diaper product 115 that can be constructed using the film of the present invention. The diaper 115 has a layer of perforated thermoplastic film 79 that is positioned over an absorbent core 117. The film 79 is positioned so that the ends of the capillaries 83 that extend from the film are in contact with the absorbent core 117. The absorbent core can include one or more layers of a non-woven material 119 and a highly absorbent wadding or gel material 121. A non-pervious thermoplastic film 123 is positioned on the side of the absorbent core 117 that is opposite to the film 79, It should be noted that the film layer 79 shown in FIGS. 19–22 will provide masking for fluid that is retained in the absorbent core material as previously discussed. It should be understood that a film similar to the films shown in the other Figures herein can also be used as the film 79 in the applications shown in FIGS. 16–22.

FIGS. 23–26 show further embodiments for a screen to form a perforated plastic film. The screens shown in FIGS. 23–26 are comprised of a unitary structure made of a single thickness of material. In certain embodiments, the sheet forming the screen is bonded together at preferred contact points and thereafter rolled to form a tubular or cylindrical shape wherein its free edges are bonded to one another to form a continuous structure. In other embodiments, the screen is a seamless cylinder and is formed in a suitable manner. In a preferred embodiment, the thickness of the screen ranges from about 10 to about 100 mils thick and preferably about 25 mils thickness.

FIG. 23 shows a screen 214 having an outer surface 239 that is disposed to be in contact with a thermoplastic material 217 and an inner surface 240 that faces a vacuum chamber (not shown). The outer surface 239 defines a plurality of apertures 241. The inner surface 240 also defines a plurality of apertures 242. The apertures 241 and 242 are in communication to form a passageway 245 which extends through the screen 214.

In preferred embodiments, the effective diameter of the apertures 241 and 242 can range from about 2 mils to 100 mils. In practice, it is found that a range from about 7 mils to about 60 mils works particularly well.

As shown in FIG. 23, the apertures 241 are circumferentially displaced from the apertures 242 such that the passageway 245 is disposed at an angle. The apertures 241 and 242 shown in FIG. 23 have substantially the same diameter. This results in the passageway 245 being disposed at an angle from about 5° to about 60° with respect to a plane or line 247 which extends perpendicular to the outer surface 239 of the screen 214. This angle is generally shown as angle A in FIG. 23.

In FIG. 23, the apertures 241 and 242 are generally circular in shape and the passageway 245 formed through the screen 214 is generally cylindrical in shape. However, it should be understood that shapes for the apertures can vary and that oval, ellipsoidal and other shapes can be used, and that multi-sided figures such as a rectangle, square, hexagon or pentagon can be used for the apertures 241 and 242. In other embodiments, the apertures 241 have a substantially different geometric shape from the apertures 242 such that the passageway 245 gradually changes dimensions as it extends from the outer surface 239 to the inner surface 240, in a manner similar to the screen shown in FIGS. 5A and 5B described above.

Referring again to FIG. 23, a film 217 formed using the screen 214 is generally shown. The film 217 has a first surface 220 and a second surface 222. The first and second surfaces 220 and 222 of the film 217 are in substantially parallel relationship. The film 217 has a plurality of perforations 230 which extend from the first planar surface 220 and define the second or three-dimensional surface 222. Each perforation 230 forms a capillary 232 that is displaced at the angle A from about 5° to about 60° with respect to the plane 247. In the embodiment shown, the capillaries 232 are substantially cylindrical in shape and have a side wall 234 which defines a passageway 236. The passageway 236 has the first opening 230 in the surface 220 of the film and a second opening 231 at an end 237 of the capillary 232 that is spaced apart from the surface 220 of the film 217. The ends 237 of the capillaries 232 are usually spaced apart from the surface 220 of the film 217 by a distance of about 0.005 to about 0.5 of an inch with a spacing from about 0.007 to about 0.012 of an inch being preferred. The opening 230 has a centerpoint $P_1$ and the opening 231 has a centerpoint $P_2$. In certain embodiments, the centerpoint $P_1$ of the opening 230 is displaced from the centerpoint $P_2$ of the opening 231 by a distance that is from about 5% to about 200% of the diameter of the opening 231. The preferred distance of the centerpoint $P_1$ from the centerpoint $P_2$ is preferably from about 75% to 125% of the diameter of the opening 231. As can be seen in FIG. 23, the capillaries 232 substantially prevent a direct line of sight from the first surface 220 to the second surface 222 of the film 217.

Another embodiment is shown in FIG. 24, wherein a screen 314 has an outside surface 339 and an inside surface 340. The outside surface 339 has a plurality of apertures 341. The inside surface 340 has a plurality of apertures 342. The apertures 341 and 342 are in communication to form a passageway 345. The passageway 345 becomes progressively smaller as the passageway 345 extends from the aperture 341 to the aperture 342. In this screen structure, the passageway 345 that is formed will converge as the passageway 345 advances through the screen 314. In this particular structure, the passageway 345 continuously and uniformly converges as the passageway 345 advances to the screen 314.

Still another embodiment is shown in FIG. 25, wherein a screen 414 has an outside surface 439 and inside surface 440. The outside surface 439 defines a plurality of apertures 441. The inside surface 440 defines a plurality of apertures 442. The apertures 441 and 442 are in communication to form a passageway 445. In FIG. 25, the passageway 445 becomes progressively smaller as the passageway 445 extends from the aperture 441 to the aperture 442. The passageway 445 converges in one direction as the passageway advances through the screen 414.

Still another embodiment is shown in FIG. 25A, wherein a screen 414' has an outside surface 439' and an inside surface 440'. The outside surface 439' defines a plurality of apertures 441' The inside surface 440' defines a plurality of apertures 442'. The apertures 441' and 442' are in communication to form a passageway 445'. In FIG. 26, the passageway 445' becomes progressively larger as the passageway extends from the aperture 441' to the aperture 442'. The passageway 445' diverges in one direction as the passageway advances through the screen 414'.

Still another embodiment is shown in FIG. 26, wherein a screen 514 defines an outside surface 539 and inside surface 540. The outside surface 539 defines a plurality of apertures 541. In the inside surface 540 defines a plurality of apertures 542. The apertures 541 and 542 are in communication to form a passageway 545. The passageway 545 has a first portion 551 which is disposed in one direction and a second portion 553 which is disposed in an opposite direction. The first portion 551 of the passageway 545 is disposed at an angle A that is from about 5° to about 60° with respect to a line or plane 547 which extends perpendicular to the outer surface 539 of the screen 514. The second portion 553 is disposed at an angle B that is from about 5° to about 60° with respect to the plane or line 547.

The films produced on the screens described above have capillaries that are disposed at an angle that acts to block a direct line of sight (that is perpendicular to the surface of the film) through the apertures. Accordingly, the films produced using the screens will have a masking characteristic such that fluids that pass through the film to an absorbent structure adjacent the second surface of the film will not be as visible to an end user as when the capillaries are perpendicular to the first surface of the film.

The above description of the invention is given for the sake of explanation and various modifications and substitutions, other than those cited, can be made without departing from the scope of the following claims.

I claim:

1. A cylindrical screen for perforating a thermoplastic film comprising:

the cylindrical screen comprising a single thickness of a material having an outer surface and an inner surface;

the screen having a plurality of outer apertures and inner apertures, each outer aperture extending from the outer surface of the screen and terminating at the corresponding inner aperture on the inner surface of the screen; and each of the outer and inner apertures defining a slanted passageway through the screen, the passageway being disposed at an acute angle A from about 5° to about 60°, the angle A being defined between a first line drawn through a center of the passageway and a second line disposed substantially perpendicular to the outer surface of the screen, the passageways preventing a direct line of sight along the second line.

2. The screen of claim 1, wherein the single thickness of material is a sheet formed into a cylindrical shape.

3. The screen of claim 1, wherein the single thickness of material is a seamless cylinder.

4. The screen of claim 1, wherein the inner apertures and the outer apertures are substantially circular and the passageways are substantially cylindrical.

5. The screen of claim 1, wherein the outer apertures are substantially the same shape as the inner apertures.

6. The screen of claim 1, wherein the outer apertures have a substantially different geometrical shape from the inner apertures.

7. The screen of claim 1, wherein the outer apertures vary in size from the inner apertures, whereby the passageways converge as the passageways extend through the screen.

8. The screen of claim 1, wherein the outer apertures vary in size from the inner apertures, whereby the passageways diverge as the passageway extend through the screen.

9. The screen of claim 1, wherein the passageway has a first portion which is disposed at the angle A from about 5° to about 60°, and further has a second portion that is disposed at an angle B from about 5° to about 60° wherein the acute angle B is defined between a third line drawn through a center of the passageway in the second portion and the second line disposed substantially perpendicular to the outer surface of the screen, the second portion extending in a direction substantially opposite to the first portion and preventing a direct line of sight along the second line.

10. The screen of claim 1, wherein the screen has a thickness from about 10 to about 100 mils.

11. The screen of claim 10, wherein the screen has a thickness of about 25 mils.

12. The screen of claim 1, wherein the apertures have a diameter from about 2 to about 100 mils.

13. The screen of claim 12, wherein the apertures have a diameter from about 7 to about 60 mils.

14. A laminated cylindrical screen for perforating a thermoplastic film comprising:

two or more relatively thin sheets secured together to form a cylindrical shape; and a plurality of apertures positioned in each of the sheets, the apertures in one sheet having a different geometrical shape than apertures in adjacent sheets, centers of the apertures in one sheet being circumferentially displaced in the same direction with respect to centers of apertures of the adjacent sheet to form slanted passageways through the screen, the passageways being disposed at an acute angle A which is defined between a first line drawn through the centers of apertures of adjacent sheets and a second line disposed substantially perpendicular to a surface of the screen, the passageways preventing a direct line of sight along the second line.

15. The screen of claim 14, wherein the apertures on adjacent sheets are displaced a distance from about 1% to about 50% of a diameter of the apertures in one sheet from the apertures in adjacent sheets.

16. The screen of claim 15, wherein the apertures in one sheet are displaced a distance from about 5% to about 25% of the diameter of the apertures from the apertures in adjacent sheets.

17. The screen of claim 14, wherein the acute angle A is from about 5° to about 60°.

18. The screen of claim 14, wherein the apertures in an outermost sheet of the screen have a substantially hexagon shape and the apertures in an innermost sheet of the screen have a substantially circular shape.

19. The screen of claim 14, wherein the apertures in the sheets vary in size, whereby the passageways converge as the passageways extend through the screen.

20. The screen of claim 14, wherein the apertures in the sheets vary in size, whereby the passageways diverge as the passageways extend through the screen.

21. The screen of claim 17, wherein the passageways have first portions where the apertures are disposed at the angle A, and second portions that are disposed at an acute angle B of from about 5° to about 60° wherein the angle B is defined between a third line drawn through the centers of the apertures in the second portion and the second line disposed substantially perpendicular to the surface of the screen, the second portions extending in a direction substantially opposite to the first portions.

22. The screen of claim 14, wherein the sheets have a thickness from about 1 to about 5 mils.

23. The screen of claim 22, wherein the sheets have a thickness of about 2 mils.

24. The screen of claim 14, wherein from about 2 to about 20 sheets are used to form the screen.

25. The screen of claim 14, wherein from about 4 to about 10 sheets are used to form the screen.

26. The screen of claim 14, wherein the apertures have a diameter from about 2 to about 100 mils.

27. The screen of claim 14, wherein the apertures have a diameter from about 7 to about 60 mils.

* * * * *